United States Patent
Barakat et al.

(10) Patent No.: US 11,589,934 B2
(45) Date of Patent: Feb. 28, 2023

(54) EFFICIENT BRAKE BOOST FOR MECHATRONIC ARTICULABLE ARM

(71) Applicant: Brainlab AG, Munich (DE)

(72) Inventors: Mohamed Ahmed Fouad Barakat, Munich (DE); Nils Frielinghaus, Heimstetten (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/497,853

(22) PCT Filed: Sep. 24, 2018

(86) PCT No.: PCT/EP2018/075743
§ 371 (c)(1),
(2) Date: Sep. 26, 2019

(87) PCT Pub. No.: WO2020/064077
PCT Pub. Date: Apr. 2, 2020

(65) Prior Publication Data
US 2021/0330401 A1 Oct. 28, 2021

(51) Int. Cl.
*A61B 34/30* (2016.01)
*A61B 34/20* (2016.01)
*A61B 90/50* (2016.01)
*G16H 40/63* (2018.01)

(52) U.S. Cl.
CPC .............. *A61B 34/30* (2016.02); *A61B 34/20* (2016.02); *A61B 90/50* (2016.02); *G16H 40/63* (2018.01); *A61B 2034/2055* (2016.02); *A61B 2090/508* (2016.02)

(58) Field of Classification Search
CPC ....... A61B 34/20; A61B 34/30; A61B 19/201; A61B 19/203; A61B 19/5244; A61B 90/50
See application file for complete search history.

(56) References Cited

U.S. PATENT DOCUMENTS

| | | | |
|---|---|---|---|
| 4,592,352 A * | 6/1986 | Patil | A61B 90/11 5/637 |
| 5,695,500 A * | 12/1997 | Taylor | B25J 9/04 606/130 |
| 6,642,686 B1 | 11/2003 | Ruch | |
| 2013/0053866 A1 | 2/2013 | Leung et al. | |
| 2018/0008358 A1 | 1/2018 | Kostrzewski | |
| 2018/0078320 A1 | 3/2018 | Griffiths | |

OTHER PUBLICATIONS

International Search Report for corresponding international application No. PCT/EP2018/075743, dated May 17, 2019. 11 pages.

* cited by examiner

*Primary Examiner* — Vi X Nguyen
(74) *Attorney, Agent, or Firm* — Tucker Ellis LLP (57) ABSTRACT

Disclosed is a computer-implemented method of determining control data for increasing the braking force exerted by a braking mechanism of a mechatronic articulable arm on at least one or all joints connecting the arm elements of the mechatronic articulable arm to a level of braking force which is higher than the level required for locking the joint or joints, respectively. The control data is determined in dependence on both the relative position between the mechatronic articulable arm and an anatomical body part of patient, and a locking state of the mechatronic articulable arm.

20 Claims, 5 Drawing Sheets

EFFICIENT BRAKE BOOST FOR MECHATRONIC ARTICULABLE ARM

RELATED APPLICATION DATA

This application is a national phase application of International Application No. PCT/EP2018/075743 filed Sep. 24, 2018, the contents of which are incorporated herein by reference.

FIELD OF THE INVENTION

The present invention relates to a computer-implemented method of determining control data for controlling a brake mechanism of a medical robotic system and a corresponding computer program, a computer-readable program storage medium storing such a program and a computer for executing the program, as well as a medical system comprising the aforementioned computer.

TECHNICAL BACKGROUND

In the state of the art, it is known to activate a braking mechanism of a mechatronic articulable arm usable for medical purposes for decreasing the movability of the joints connecting the arm elements in dependence on the distance between the mechatronic articulable arm (for example, its manipulator and/or an instrument attached to it) and a patient's body. Using a brake boosting mechanism for increasing the rigidity of the mechatronic articulable arm which is desired under specific circumstances however leads to a substantial increase in heat generated by the braking mechanism when the braking force to be exerted is boosted only in dependence on the aforementioned distance.

The present invention has the object of for example providing a method for enabling brake boost while maintaining energetic efficiency.

The present invention can be used for medical procedures e.g. in connection with a medical robotic system such as the CIRQ system, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses determining control data for increasing the braking force exerted by a braking mechanism of a mechatronic articulable arm on at least one or all joints connecting the arm elements of the mechatronic articulable arm to a level of braking force which is higher than the level required for locking the joint or joints, respectively. The control data is determined in dependence on both the relative position between the mechatronic articulable arm and an anatomical body part of patient, and a locking state of the mechatronic articulable arm.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining control data for controlling a brake mechanism of a medical robotic system comprising a mechatronic articulable arm including at least one joint. The mechatronic articulable arm is for example a passive mechatronic arm, but the invention may also be applied to an active mechatronic articulable arm. The brake mechanism includes at least one brake, for example electromagnetic or electromechanical brake, for braking a movement of the at least one joint.

An active mechatronic articulable arm includes at least one motor (actuator) for actuating (moving) the mechatronic articulable arm, for example changing its joint configuration which is defined for example by a set of at least one joint state which may in turn be defined by an angle formed by the joint. A passive mechatronic articulable arm is a hybrid of a traditional holding arm and a classical robotic arm in the way that it offers all features of a robotic arm except for the at least one motor which is replaced, for the passive mechatronic articulable arm, by human labour. The removal of the motors allows to come up with a much simpler, lighter and safer device.

The mechatronic articulable arm with which the method according to the first aspect may be used is for example part of a robotic or semi-robotic system. A robotic system is understood to be a system which conducts operations exclusively on the basis of electronic commands received e.g. from or via a computer. A semi-robotic system is understood to be a system which conducts operations on the basis of both manual user intervention (e.g. for positioning at least a part of the system such as at least part of the mechatronic articulable arm) and electronic commands received e.g. from or via a computer. The mechatronic articulable arm comprises a plurality (i.e. at least two) arm elements which are connected to each other by at least one joint such as a turning joint or hinge and thus form connected elements of the mechatronic articulable arm. The connected elements can be moved relative to one another for example by rotating them (i.e. neighbouring elements) relative to one another (specifically, if they are connected via a turning joint, i.e. a swivel joint) around at least substantially around their longitudinal axes or by articulating them (i.e. neighbouring elements) relative to one another (specifically if they are connected via a hinge, for example articulating them relative to one another at an angle allowed by the hinge). Each connected element has a generally elongate shape and is for example rigid. In one example, a utility element (within this disclosure also called manipulator) comprises at least one of a medical tool or a fastening unit for fastening a medical tool is attached (e.g. operably coupled) to or included in the mechatronic articulable arm at the free (distal) end of the mechatronic articulable arm.

The method comprises executing, on at least one processor of at least one computer (for example at least one computer being part of the navigation system), the following exemplary steps which are executed by the at least one processor.

In a (for example first) exemplary step, body part position data is acquired which describes a position of an anatomical body part of a patient. The anatomical body part may essentially be any body part and in an example is at least part of the head or a limb. In one example, the body part position data is or has been generated by tracking a marker device such as a reference star which is attached at a predetermined (i.e. at least one of known or fixed) position to the anatomical body part. The tracking is for example implemented as optical tracking using a navigation system using reflection of infrared radiation from retroreflective markers (such as marker spheres) or as electromagnetic tracking using detection of electromagnetic radiation emitted by passive or active resonance coils functioning as the marker device for position determination. Alternatively or additionally to using the marker device, the position of the anatomical body part may be determined by processing of signals generated by a surface camera imaging the anatomical body part.

In a (for example second) exemplary step, mechatronic arm position data is acquired based on the body part position data. The mechatronic arm position data describes a relative position between the mechatronic articulable arm and the anatomical body part. For example, the mechatronic articulable arm of which the position is described by the mechatronic arm position data is a passive mechatronic articulable arm. In an example, the mechatronic arm position data includes information describing a distance between the mechatronic articulable arm (for example, a connected element of the mechatronic articulable arm or the utility element) and the anatomical body part. In an example of this step, mechatronic arm tracking data is acquired which describes a position of the mechatronic arm, for example a part of the mechatronic arm lying at least substantially at the distal end of the mechatronic articulable arm (such as the manipulator), in a tracking coordinate system. The mechatronic arm position data is then acquired for example based on the mechatronic arm tracking data. For example, the mechatronic arm tracking data is or has been generated by (e.g. optically) tracking a marker device (e.g. a reference star) which is attached, for example at a predetermined (i.e. at least one of known or fixed) position, to the mechatronic articulable arm. Alternatively or additionally, the mechatronic arm tracking data in an example is or has been generated by evaluating an electronic signal generated by at least one encoder configured to encode the joint state (for example, the joint angle) of the at least one joint. For example, the mechatronic articulable arm comprises a manipulator such as a medical instrument. The manipulator is for example attached detachably or non-detachably to an at least substantially distal end of the mechatronic articulable arm and wherein the mechatronic arm position data describes a relative position between the manipulator and the anatomical body part.

In a (for example third) exemplary step, brake modulation data is determined based on the mechatronic arm position data, wherein the brake modulation data is determined to describe at least one electronic control signal to be issued to the medical robotic system for modulating a braking force to be applied by a brake mechanism of the mechatronic articulable arm while the at least one joint is being kept in a locked state. In the locked state, movement of the joint, for example a change of its joint state, is prohibited (i.e. rendered at least substantially impossible). For example, the mechatronic arm position data is analysed to determine whether the spatial relationship, for example the relative position, between the anatomical body part and the mechatronic articulable arm fulfils a predetermined condition, for example whether it fulfils a predetermined relationship (such as being less than or greater than a predetermined threshold distance). Depending on the result of that analysis, the brake modulation data is determined or for example not determined, respectively. For example, the brake modulation data is determined to describe an increase in the braking force to a value greater than a braking force applied by the braking mechanism to effect only (i.e. nor more than but at least) the locked state (a so-called locking force). Notably, the brake mechanism also effects the locked state by applying a predetermined force to the at least one joint which prohibits a movement of the joint, for example a change of its joint state. The increase to the braking force larger than the locking force may originate from a force value lower than the locking force (e.g. from a force value of zero) or may embody a further increase from a force value already larger than the locking force. Increasing the braking force to a value larger than the locking force (also called "brake boosting") leads to increased rigidity of the mechatronic articulable arm for example in a situation in which the manipulator is desirably kept reliably at a constant position, for example when conducting a medical procedure using the manipulator for example on the anatomical body part. The value to which the braking force shall be increased may for example be up to 130% or at least substantially or exactly 130% or at least substantially or exactly 150% or lie in an interval ranging from 110% to 150% of the locking force. Making activation of brake boosting dependent on the spatial relationship between the mechatronic articulable arm and the anatomical body part limits the heat production caused by applying the increased braking force to situations where brake boosting is actually desirable. Due to this limitation of heat production, the risk of damaging for example by burning the patient, medical personnel or equipment is reduced. The brake boosting, i.e. the increased value of the braking force, in one example is dependent on the actual joint configuration of the mechatronic articulable arm. Alternatively or additionally, the brake boosting may be calculated individually for each joint included in the mechatronic articulable arm, for example in dependence on its joint state.

In an example of the method according to the first aspect, the brake modulation data is determined to describe an increase in the braking force if (e.g. only if) the at least one joint is in the locked state, for example if it has been determined that the at least one joint is in the locked state. To this end, for example mechatronic arm locking state data is acquired which describes the locking state of the at least one joint, for example whether the at least one joint is or shall be in a locked state or for example the at least one joint is not or shall not be in a locked state. The mechatronic arm locking state data is analysed to determine whether it describes that the at least one joint is in a locked state. The brake modulation data is then determined to describe an increase in the braking force (for example only) if the result of analysing the mechatronic arm locking state data is that the mechatronic arm locking state data describes that the at least one joint is in a locked state. The locking state of the at least one joint may be automatically observed to decide whether the increased braking force still needs to be applied. For example, the brake modulation data is determined to describe at least one electronic control signal to be issued to the medical robotic system for decreasing the braking force (for example for decreasing the braking force to no more than the locking force) if the result of analysing the mechatronic arm locking state data is that the mechatronic arm locking state data describes that the at least one joint shall not be or is not in a locked state.

In a second aspect, the invention is direct to a medical method of controlling a brake mechanism of a medical robotic system comprising a mechatronic articulable arm including at least one joint, the method comprising executing the method according to any one of the preceding claims, and issuing, to the medical robotic system, the electronic control signal for modulating the braking force.

In a third aspect, the invention is directed to a computer program which, when running on at least one processor (for example, a processor) of at least one computer (for example, a set of computers comprising at least one computer, for example exactly one computer or a plurality of computers such as exactly two computers or a data processing network comprising at least two computers) or when loaded into at least one memory (for example, a memory) of at least one computer (for example, a set of computers comprising at least one computer, for example exactly one computer or a plurality of computers such as exactly two computers or a data processing network comprising at least two computers), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a fourth aspect, the invention is directed to a for example non-transitory computer-readable program storage medium on which the program according to the third aspect is stored.

In a fifth aspect, the invention is directed to a set of computers, each of the computers comprising at least one processor (for example, a processor) and at least one memory (for example, a memory), wherein the program according to the third aspect is running on the processor or is loaded into the memory, or wherein the at least one computer comprises the computer-readable program storage medium according to the fourth aspect. The set of computers comprises at least one computer, for example exactly one computer or a plurality of computers such as exactly two computers or a data processing network comprising at least two computers. Alternatively or additionally, the invention according to the fifth aspect is directed to a for example non-transitory computer-readable program storage medium storing a program for causing the computer according to the fifth aspect to execute the data processing steps of the method according to the first aspect.

In a sixth aspect, the invention is directed to a medical robotic system, comprising:
a) the set of computers according to the fifth aspect;
b) at least one body part tracking device (e.g. a camera or electromagnetic detection device of a medical navigation system) configured to generate an electronic signal usable to generate the body part position data;
c) at least one arm tracking device (e.g. a camera of a medical navigation system and/or at least one encoder for encoding the joint state of the at least one joint) configured to generate an electronic signal usable to generate the mechatronic arm position data; and
d) the mechatronic articulable arm including at least one joint and a brake mechanism,
wherein the at least one computer is operably coupled to
the at least one body part tracking device for acquiring, on the basis of the electronic signal generated by the at least one body part tracking device, the body part position data,
the at least one arm tracking device for acquiring, on the basis of the electronic signal generated by the at least one arm tracking device, the mechatronic arm position data, and
the mechatronic articulable arm for sending, to the mechatronic articulable arm and on the basis of the brake activation data, at least one electronic signal to cause the brake mechanism to be activated.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise (in particular does not require or imply) a step of using the manipulator after conducting surgical activity for example on the anatomical body part. More particularly, the invention does not involve or in particular comprise or encompass any surgical or therapeutic activity. The invention is instead directed as applicable to allowing controlling the functionality and/or operating the brake mechanism of the mechatronic articulable arm. For this reason alone, no surgical or therapeutic activity and in particular no surgical or therapeutic step is necessitated or implied by carrying out the invention.

The present invention also relates to the use of the system according to the preceding claim for determining control data for controlling a brake mechanism of a medical robotic system comprising a mechatronic articulable arm including at least one joint, wherein the use comprises execution of the steps of the method according to any one of the preceding method claims for determining the control data.

Definitions

In this section, definitions for specific terminology used in this disclosure are offered which also form part of the present disclosure.

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a medical navigation system such as a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical body part which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A medical navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
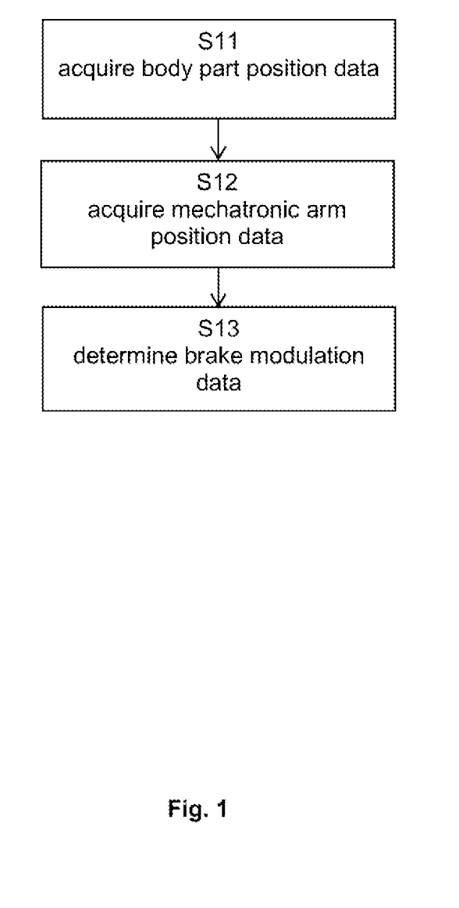
FIG. 1 illustrates the basic steps of the method according to the first aspect.

FIG. 1 illustrates the basic steps of the method according to the first aspect, in which step S11 encompasses acquiring the body part position data, step S12 encompasses acquiring the mechatronic arm position data and subsequent step S13 encompasses determining the brake modulation data.

Figure 2:
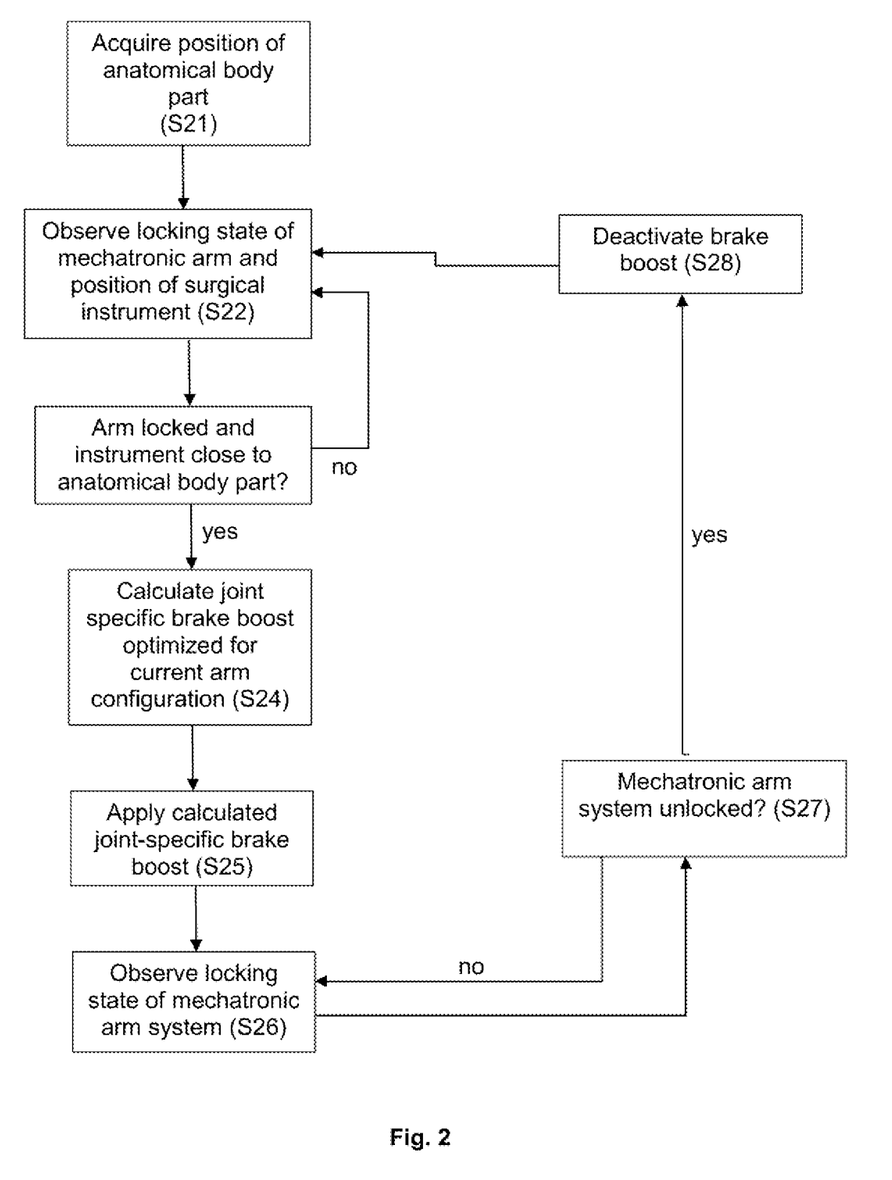
FIG. 2 shows an example of the method according to the first aspect.

FIG. 2 describes an example of the method according to the first aspect. In step S21, the position of the anatomical body part is acquired, corresponding to acquisition of the body part position data. In step S22, the locking state of the mechatronic articulable arm is observed, corresponding to acquisition of the mechatronic arm locking state data. The mechatronic arm locking state data is analysed in step S23 to determine whether the mechatronic articulable arm (for example, the at least one joint) is locked and the instrument (or manipulator, respectively) is close to the anatomical body part, for example has less than a predetermined distance from the anatomical body part. If it is determined that this is not the case (no after step S23), the method returns to execution of step S22. If step 23 results in that the analysed conditions are met (yes after step S23), the method continues with execution of step S24 which includes calculation of specific brake boost value for increasing the braking force for a current arm configuration. The increased braking force value may also be joint-specific, and may as such be applied in step S25. In subsequent step S26, the locking state is again observed, and the resulting mechatronic arm locking state data is analysed in step S27 as to whether it describes that the mechatronic arm is unlocked. If it is determined that this is not the case (no after step S27), the method returns to execution of step S27. If step S27 results in that the mechatronic arm locking state data describes that the mechatronic articulable arm (for example, the at least one joint) is in an unlocked state (yes after step S27), the method continues with execution of step S28 which relates to deactivation of the brake boost by issuing an electronic signal to the mechatronic articulable arm for reducing the braking force to at maximum the locking force at most i.e. to no more than the locking force).

Figure 3:
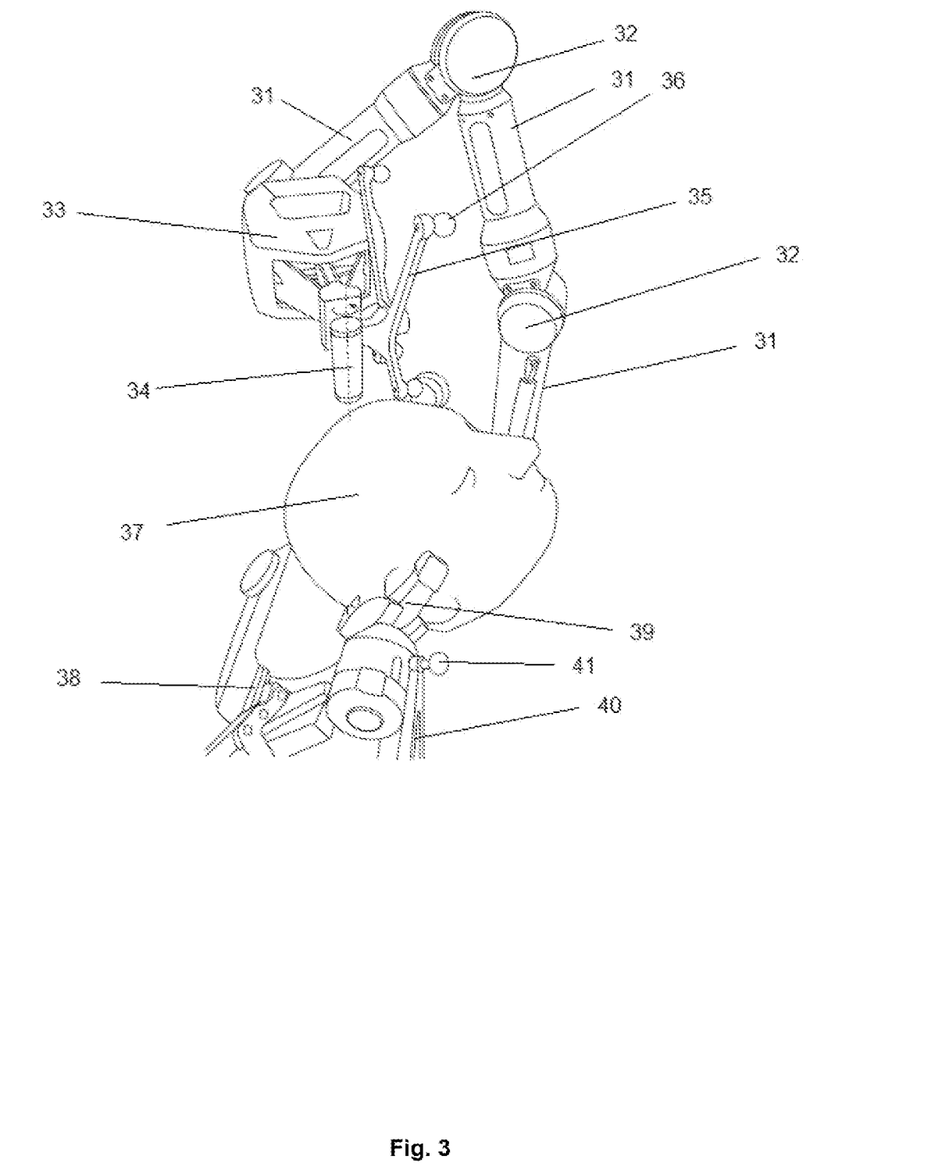
FIGS. 3 and 4 illustrate setups of the mechatronic articulable arm and the anatomical body part and two different manipulators.

FIG. 3 illustrates a first setup of the mechatronic articulable arm having a manipulator of a first type. The mechatronic articulable arm comprises connected elements 31 which are connected by joints 32 and a manipulator 33 to which an instrument 34 is attached at the distal end of the mechatronic articulable arm. Also attached to the distal end (for example, the manipulator 33) is a reference star 35 comprising markers marker spheres 36. A patient's head 37 resembling the anatomical body part is held by a holding section 39 of a clamping device 38 to which also a reference star 40 (shown only partially) having markers spheres 41 is attached so that the position of the head 37 relative to the reference star 40 is known. The instrument 34 can now be navigated—for example, its position relative to the head 37 can be determined by a navigation system. Depending on whether the joints 32 are lock and depending on at least one of the relative position or the distance between at least one of the mechatronic articulable arm or the instrument 37 and the head 37, the brake boosting is activated or deactivated.

Figure 4:
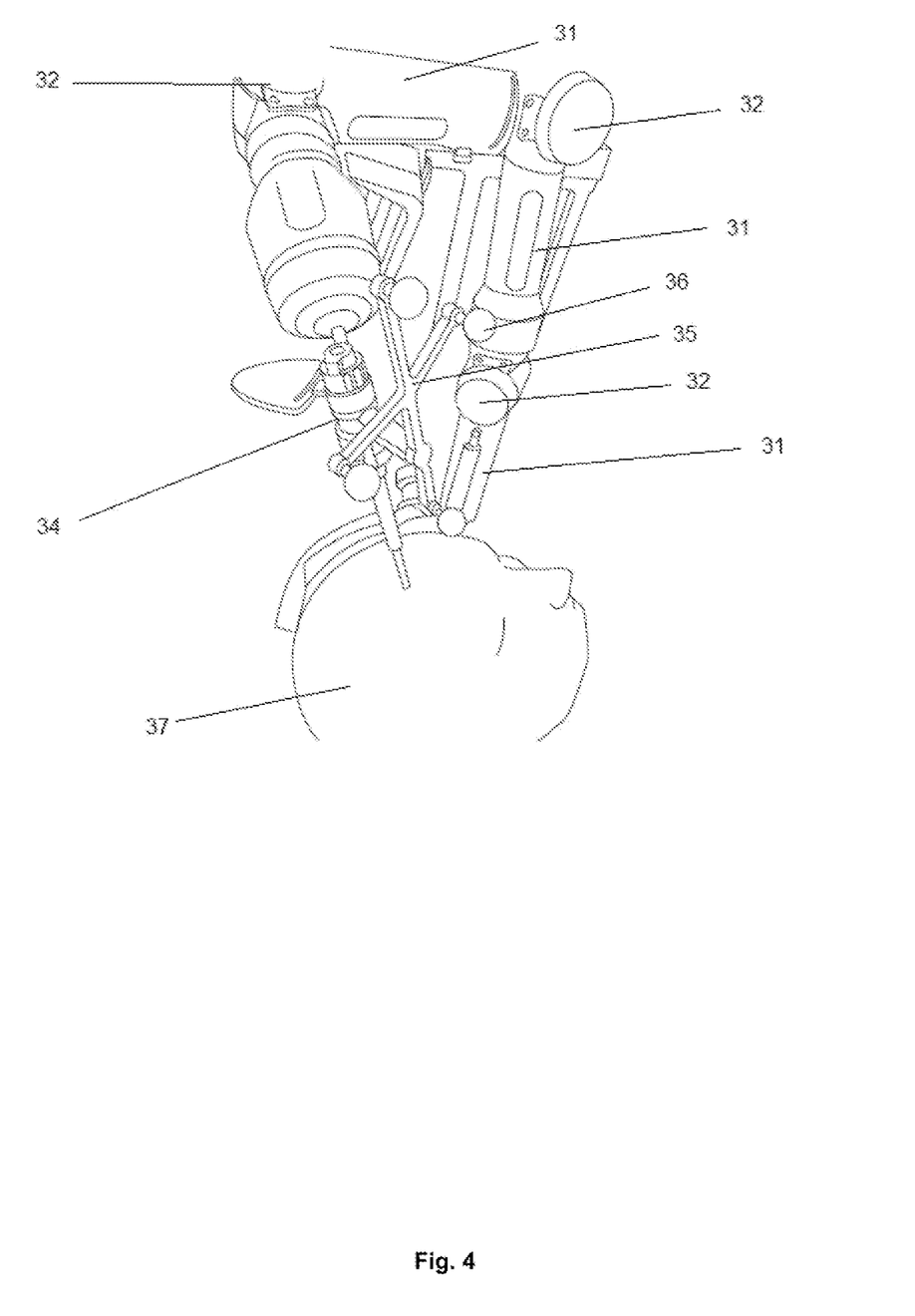

FIG. 4 illustrates a second setup of the mechatronic articulable arm having a manipulator of a second type. The same reference signs as used in FIG. 3 denote the same entities as explained in the context of FIG. 3. The instrument in this case is a drill, and the position of the patient's head 37 is not acquired via a reference star but by surface scanning using a laser scanning device and a stereoscopic camera for detecting the reflection of the laser scanning light from the surface of the head. Otherwise, the setup provides for the same functionality as the setup shown in FIG. 3.

Figure 5:
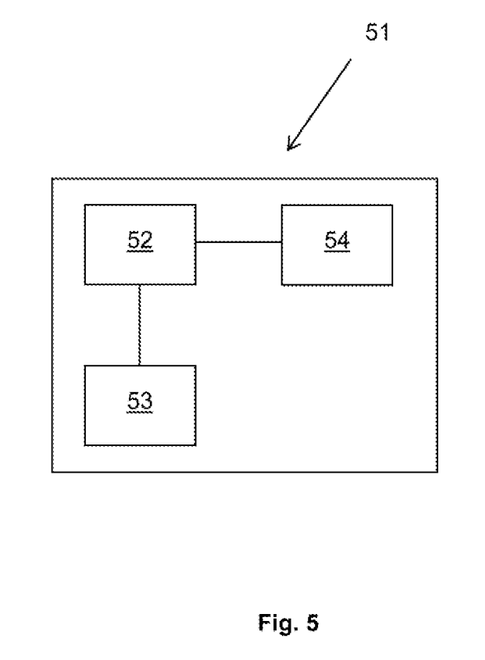
FIG. 5 is a schematic illustration of the system according to the sixth aspect.

FIG. 5 is a schematic illustration of the medical system 51 according to the fifth aspect. The system is in its entirety identified by reference sign 51 and comprises the set of computers 52, the at least one body part tracking device 53, the at least one arm tracking device 54 and the mechatronic articulable arm 55. The components of the medical system 1 have the functionalities and properties explained above with regard to the sixth aspect of this disclosure.

Further features of the disclosed invention are described in the following.

The idea is to make the brake boost adaptive in the sense that it is switched off if the current position of the instrument is not critical and to switch it on as soon as the navigation system knows that the instrument attached to the robotic hand is used.

Potential triggers for the onset (activation) of the brake boost are:
navigated instrument is close to target and the robotic end-effector is directed towards the target.
navigated instrument without robotic end-effector is close to target
depth-tracked instrument (like biopsy needle, drill guide or scalpel) is tracked close to the navigated guiding tube
position of robot base is known and arm position is close to anatomy
tracking system or position sensors indicate slipping of the arm
tracking system identifies that there is a movement at the distal end while the arm still is at the same position indicating that a force is applied Potential triggers for stopping (deactivating) the brake boost are:
navigated instrument is known to be away from patient anatomy
arm is unlocked and locked again in a position where the navigated instrument is not seen or away from the target such that the robotic end-effector is not aligned
position of robot base is known and arm position is away from the patient anatomy
navigated or depth-tracked instrument is not detected for a certain time-period
tracking system no longer indicating that any force is applied
new workflow step is activated in the navigation software Furthermore, the intensity of the brake boost can be modulated such that it is different for each joint. In the most simple embodiment, the brake boost could have pre-defined values for each joint depending on the joint type and position in the kinematic chain (e.g. joints that are rotated around the gravity direction do not need any boost at all, whereas the weakest joints with a lot of gravity acting upon them require the most boost).

In more complex embodiments, one can modulate the brake boost depending on the current arm configuration and/or the expected forces applied to the arm.

Typically, the most important force component is gravity that acts upon the robotic system itself. The torque exerted by gravity on each rotational joint can be approximated by the length of the lever arm to the center of gravity perpendicular to the rotational axis and the component of the gravitational force that acts on it which depends on the angle of the axis towards the direction of gravity. To do that, one can first aggregate the centers of gravity and weights of the more distal arm segments as well as the end-effector and clinical instruments. Similarly, one can determine the torque exerted by dynamic forces (typically applied to the distal end of the arm) that the system is supposed to withstand. With this information, one can compare the torque resulting from gravitational plus dynamic forces to the braking power of each joint and define a required boost level based on the pre-determined characteristics of the braking system. An alternative approach is to define a certain energy budget for the brake boost and to distribute this budget to the different joints such that the joint with the least remaining torque head room receives the maximum boost.

The invention claimed is:

1. A computer-implemented medical method of determining control data for controlling a brake mechanism of a medical robotic system that comprises a mechatronic articulable arm including at least one joint, the method comprising
acquiring, at a computer, body part position data describing a position of an anatomical body part of an associated patient;
acquiring, at the computer and based on the body part position data, mechatronic arm position data, the mechatronic arm position data describing a relative position between the mechatronic articulable arm and the anatomical body part; and determining, by the computer and based on the mechatronic arm position data, brake modulation data, the brake modulation data describing at least one electronic control signal to be issued to the medical robotic system for increasing a braking force to be applied by a brake mechanism of the mechatronic articulable arm while the at least one joint is being kept in a locked state to a value larger than a locking force.

2. The method according to claim 1, further comprising:
acquiring, at the computer, mechatronic arm locking state data describing whether the at least one joint is or shall be in a locked state;
analyzing, by the computer, the mechatronic arm locking state data to determine whether the mechatronic arm locking state data describes that the at least one joint is in a locked state,
wherein the brake modulation data is determined to describe an increase in the braking force in a condition that the analyzing the mechatronic arm locking state data determines that the at least one joint is in a locked state.

3. The method according to claim 2, wherein the brake modulation data is determined to describe at least one electronic control signal to be issued to the medical robotic system for decreasing the braking force in a condition that the analyzing the mechatronic arm locking state data determines that the at least one joint shall not be or is not in a locked state.

4. The method according to claim 1, further comprising:
acquiring, at the computer, mechatronic arm tracking data that describes a position of the mechatronic articulable arm, in a tracking coordinate system, the mechatronic arm position data being acquired based on the mechatronic arm tracking data.

5. The method according to claim 4, further comprising:
tracking, by an arm tracking device operably associated with the computer, an arm marker device attached to the mechatronic articulable arm; and
generating, by the arm tracking device, the mechatronic arm tracking data based on the tracked arm marker device.

6. The method according to claim 5, wherein the arm marker device is attached at a predetermined position of the mechatronic articulable arm.

7. The method according to claim 4, further comprising:
generating, by at least one encoder configured to encode a joint state of the at least one joint, an electronic signal, the at least one encoder being operably associated with the computer; and
generating, by the computer based on an evaluation of the electronic signal from the at least one encoder, the mechatronic arm tracking data.

8. The method according to claim 4, wherein the position of the mechatronic articulable arm is based on a part of the mechatronic articulable arm lying at least substantially at the distal end of the mechatronic articulable arm.

9. The method according to claim 1, further comprising:
tracking, by a body part tracking device operably associated with the computer, a body part marker device attached at a predetermined position to the anatomical body part; and
generating, by the body part tracking device based on the tracked body part marker device, the body part position data.

10. The method according to claim 1, wherein the mechatronic articulable arm comprises a manipulator that is attached detachably or non-detachably to an at least substantially distal end of the mechatronic articulable arm.

11. The method according to claim 10, wherein the manipulator comprises a medical instrument.

12. The method according to claim 1, wherein the brake mechanism includes at least one brake for braking a movement of the at least one joint.

13. The method according to claim 12, wherein the at least one brake is an electromagnetic or electromechanical brake.

14. The method according to claim 1, further comprising issuing, by the computer to the medical robotic system, the electronic control signal for modulating the braking force.

15. The method according to claim 1, wherein the mechatronic articulable arm is a passive mechatronic articulable arm.

16. A non-transitory computer readable storage device storing a program which, when running on a computer or when loaded onto a computer, causes the computer to:
acquire body part position data describing a position of an anatomical body part of an associated patient;
acquire mechatronic arm position data based on the body part position data, the mechatronic arm position data describing a relative position between the mechatronic articulable arm and the anatomical body part; and
determine brake modulation data based on the mechatronic arm position data, the brake modulation data describing at least one electronic control signal to be issued to a medical robotic system for increasing a braking force to be applied by a brake mechanism of the mechatronic articulable arm while the at least one joint is being kept in a locked state to a value larger than a locking force.

17. A medical robotic system, comprising:
at least one computer;
a body part tracking device operably associated with the at least one computer;
an arm tracking device operably associated with the at least one computer; and
a mechatronic articulable arm including at least one joint and a brake mechanism, the mechatronic articulable arm being operably associated with the at least one computer,
the at least one computer being configured to:
acquire body part position data describing a position of an anatomical body part of an associated patient from the body part tracking device;
acquire mechatronic arm position data from the arm tracking device based on the body part position data, the mechatronic arm position data describing a relative position between the mechatronic articulable arm and the anatomical body part;
determine brake modulation data based on the mechatronic arm position data, the brake modulation data describing at least one electronic control signal to be issued to the brake mechanism for increasing a braking force to be applied by the brake mechanism while the at least one joint is being kept in a locked state to a value larger than a locking force; and
issue, to the mechatronic articulable arm and on the basis of the brake activation data, the at least one electronic control signal to cause the brake mechanism to be activated.

18. The system according to claim 17, wherein the at least one computer is a set of computers.

19. The system according to claim 17, further comprising a body part marker device attached at a predetermined position to the anatomical body part, the body part marker device configured to be tracked by the body part tracking device.

20. The system according to claim 17, further comprising an arm marker device attached to the mechatronic articulable arm, the arm marker device configured to be tracked by the arm tracking device.

* * * * *